US011331011B2

(12) United States Patent
Morley et al.

(10) Patent No.: US 11,331,011 B2
(45) Date of Patent: May 17, 2022

(54) SYSTEM FOR THE TRANSCUTANEOUS DETERMINING OF BLOOD ALCOHOL CONCENTRATION

(71) Applicant: Dräger Safety AG & Co. KGaA, Lübeck (DE)

(72) Inventors: Stefan Morley, Lübeck (DE); Arne Tröllsch, Lübeck (DE); Livio Fornasiero, Bliestorf (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 153 days.

(21) Appl. No.: 15/514,142

(22) PCT Filed: Sep. 24, 2015

(86) PCT No.: PCT/EP2015/001902
§ 371 (c)(1),
(2) Date: Mar. 24, 2017

(87) PCT Pub. No.: WO2016/055141
PCT Pub. Date: Apr. 14, 2016

(65) Prior Publication Data
US 2017/0296109 A1 Oct. 19, 2017

(30) Foreign Application Priority Data
Oct. 6, 2014 (DE) .................... 10 2014 014 872.6

(51) Int. Cl.
*A61B 5/1455* (2006.01)
*A61B 5/145* (2006.01)
*A61B 5/00* (2006.01)

(52) U.S. Cl.
CPC .......... *A61B 5/1455* (2013.01); *A61B 5/0075* (2013.01); *A61B 5/14546* (2013.01); *A61B 5/4845* (2013.01)

(58) Field of Classification Search
None
See application file for complete search history.

(56) References Cited

U.S. PATENT DOCUMENTS 5,573,394 A 11/1996 Pershina
5,692,504 A * 12/1997 Essenpreis ......... A61B 5/14532
356/39

(Continued)

FOREIGN PATENT DOCUMENTS

DE 69637339 T2 10/2008
EP 1995576 B1 4/2011

(Continued)

OTHER PUBLICATIONS

S. T. McCain, M. E. Gehm, Y. Wang, N. P. Pitsianis, M. Sullivan, and D. J. Brady, "Multimodal, multiplex, Raman spectroscopy of alcohol in diffuse, fluorescent media," Proceedings of SPIE, vol. 5864, (2005) (Year: 2005).*

(Continued)

*Primary Examiner* — Marjan Fardanesh
(74) *Attorney, Agent, or Firm* — McGlew and Tuttle, P.C.

(57) ABSTRACT

A system, for the transcutaneous measurement of a substance concentration, preferably alcohol, in blood, includes a light source (1); a detector device (15); an optical device (7, 7'), with an inlet (5), an outlet (49) and an exit opening (35); and a contact surface element (37) with a contact surface (41). Measuring radiation emitted by the light source (1) reaches the inlet (5) and exits the exit opening (35), to the contact surface (41). The optical device (7, 7') focuses measuring radiation at a measuring point (39) at a predefined distance from the contact surface (41). The optical device (7, 7') is configured such that scattered radiation generated in the measuring point (39) and entering into the exit opening (35) is focused at an outlet point (19) at the outlet (49). The (Continued)

detector device (15) is arranged to detect the scattered radiation focused at the outlet point (19).

14 Claims, 3 Drawing Sheets

(56) References Cited

U.S. PATENT DOCUMENTS

| | | | |
|---|---|---|---|
| 5,962,852 A * | 10/1999 | Knuettel | A61B 5/0066 |
| | | | 250/339.11 |
| 6,088,087 A | 7/2000 | Graves et al. | |
| 7,446,878 B2 | 11/2008 | Ridder et al. | |
| 7,889,349 B2 | 2/2011 | Ridder et al. | |
| 8,406,835 B2 | 3/2013 | Lucassen et al. | |
| 2004/0186382 A1* | 9/2004 | Modell | A61B 1/00059 |
| | | | 600/473 |
| 2004/0260159 A1* | 12/2004 | Gerlitz | A61B 5/14532 |
| | | | 600/319 |
| 2005/0043597 A1 | 2/2005 | Xie | |
| 2005/0200843 A1* | 9/2005 | Kumar | A61B 5/0075 |
| | | | 356/318 |
| 2006/0141429 A1 | 6/2006 | Schutte et al. | |
| 2007/0236967 A1 | 10/2007 | Liu et al. | |
| 2008/0050706 A1 | 2/2008 | Williamson et al. | |
| 2010/0168586 A1* | 7/2010 | Hillman | G02B 26/101 |
| | | | 600/476 |
| 2010/0249546 A1 | 9/2010 | White | |
| 2012/0057164 A1 | 3/2012 | Tezuka et al. | |
| 2012/0062879 A1* | 3/2012 | Spennemann | A61B 5/0059 |
| | | | 356/300 |
| 2013/0018237 A1 | 1/2013 | Henneberg et al. | |
| 2013/0278922 A1* | 10/2013 | Gelernt | G02B 21/16 |
| | | | 356/51 |
| 2014/0183362 A1* | 7/2014 | Islam | G01J 3/453 |
| | | | 250/338.4 |

FOREIGN PATENT DOCUMENTS

| | | |
|---|---|---|
| WO | 2010/085716 A1 | 7/2010 |
| WO | 2011/083111 A1 | 7/2011 |

OTHER PUBLICATIONS

Keller, Stefan [et al.]: Application of Near-Infrared-Fourier Transform Raman Spectroscopy in Medical Research. In: Journal of Raman Spectroscopy, 1994, p. 663-671, vol. 25.

Okamoto, Hideyuki [et al.]: Visible-NIR tunable Pr3+-doped fiber laser pumped by a GaN laser diode. In: Optics Express, 2009, p. 20227-20232, vol. 17, No. 22.

* cited by examiner

SYSTEM FOR THE TRANSCUTANEOUS DETERMINING OF BLOOD ALCOHOL CONCENTRATION

CROSS REFERENCE TO RELATED APPLICATIONS

This application is a United States National Phase Application of International Application PCT/EP2015/001902, filed Sep. 24, 2015, and claims the benefit of priority under 35 U.S.C. § 119 of German Application 10 2014 014 872.6, filed Oct. 6, 2014, the entire contents of which are incorporated herein by reference.

FIELD OF THE INVENTION

The present invention pertains to a system for transcutaneous determination of the concentration of a substance, preferably alcohol, in the blood.

BACKGROUND OF THE INVENTION

The blood alcohol concentration of test subjects has hitherto been determined, especially during traffic stops, invasively by taking blood. The common measurement methods are chromatography and the ADH method (alcohol dehydrogenase method). Blood must be taken from the test subject in both cases, and the blood is then analyzed according to the corresponding principle. These methods are therefore comparatively time-consuming and, in particular, not suitable for stops, in which the result is needed immediately. In particular, such methods cannot be used with so-called interlocks in motor vehicles, which only enable the vehicle to be started if it is determined before that blood alcohol concentration of the driver does not exceed a predefined limit value.

Methods have therefore been developed in which the breath alcohol concentration is determined. Using conversion methods, the alcohol content can be inferred from the breath alcohol concentration. However, the problem arises in this connection that the test subject must blow breathing air into opening for measuring the breath alcohol concentration, which is first associated with hygienic problems. This can be solved by using a new, cleaned mounted for the measuring device for each test subject. This is, however, associated, in turn, with considerable efforts.

Finally, the method of determining the blood alcohol concentration optically transcutaneously, i.e., through the skin of the test subject, was developed in the recent past as an injury-free, non-invasive method for determining the blood alcohol concentration. Light of the near or middle infrared range is radiated here into the patient's skin and the scattered light is analyzed spectrally for absorption bands of the alcohol. However, this has the technical problem that the topmost layer of the skin, namely, the epidermis, is not vascularized by blood vessels or is only vascularized to a very low extent, so that an optical measurement, which is sensitive to this topmost layer, can only yield inaccurate measured values only because of the high signal-to-noise ratio.

Only the deeper dermis and the subcutaneous tissue contain sufficient quantities of blood vessels, so that signals that make it possible to determine the blood alcohol concentration in a reliable manner can be obtained here. This means that a measuring radiation that can penetrate the skin deeper than 1 mm and preferably up to 3 mm must be used, so that scattered radiation is generated in the desired areas.

To further increase the accuracy of the measurement, it is desirable to limit the depth range in which the measurement is sensitive.

SUMMARY OF THE INVENTION

Based on the state of the art, an object of the present invention is therefore to provide a system for the transcutaneous determination of the concentration of a substance in the blood and especially for determining the blood alcohol concentration, which has a simple configuration and can yield measurement results with a higher accuracy.

According to the present invention, this object is accomplished by a system with a light source, which is configured to emit a measuring radiation, with a detector device, which is configured to detect the scattered radiation, with an optical device, which has an inlet, an outlet and an exit opening, and with a contact surface element with a contact surface, wherein the contact surface element is arranged such that measuring radiation exiting from the exit opening falls through the contact surface element, wherein the contact surface is provided on the side of the contact surface element facing away from the optical device, wherein the inlet of the optical device is arranged such that measuring radiation emitted by the light source falls on the inlet of the optical device, wherein the optical device is configured such that measuring radiation emitted from the light source and entering the inlet exits through the exit opening and is focused in a measuring point on the side of the contact surface element facing away from the optical device at a predefined distance from the contact surface, wherein the optical device is configured such that scattered radiation generated in the measuring point entering the exit opening is focused in an outlet point at the outlet, and wherein the detector device is arranged such that the detector device detects the scattered radiation focused at the outlet point.

For example, the blood alcohol concentration of a test subject can be determined with the system according to the present invention as follows. A body part of the test subject, e.g., the arm, is first arranged on the contact surface of the contact surface element adjacent to the exit opening. Measuring radiation emitted from the light source and falling on the inlet of the optical device then exits from the exit opening and falls on the skin of the patient. The measuring radiation is focused by a measuring point, which is located at a spaced location from the contact surface and hence also at a spaced location from the skin surface. This measuring point is preferably at a depth between 0.1 mm and 3 mm, especially preferably between 0.5 mm and 1 mm under the skin surface and is thus located at a spaced location from the contact surface. At the same time, the optical device is configured according to the present invention such that scattered radiation generated at this measuring point is focused at an outlet point at the outlet of the optical device.

Due to the detector device being arranged in the outlet point or due to an optical connection of the device to this outlet point via a light guide, this makes it possible to limit the area within the skin of the test subject, to which the detector device is sensitive, to the area around the measuring point.

Thus, the optical device is configured in the measuring system according to the present invention confocally in the sense that the outlet point and the measuring point are focused at the same time in the skin of the test subject.

The scattered radiation, which is focused at the outlet point and was generated essentially at the measuring point, is detected by the detector device and can be correspondingly analyzed to determine the concentration of the substance in question in the blood. This can preferably be carried out by the detector device being set up to output a spectrum (spectrum signal) of at least part of the detected scattered radiation. Such a spectrum can be analyzed for absorption bands of the substance in question, i.e., for example, alcohol. It is also conceivable, as an alternative, that the emitted spectra are compared to spectra being stored in a storage device and the blood alcohol concentration is calculated from this.

The detector device may have a grating spectrometer or a Fabry-Perot interferometer for this purpose. It is advantageous in respect to the determination of the blood alcohol concentration if the detector device is configured to bring about the spectral resolution of the scattered radiation in the range of a wavelength of 0.7 μm to 3.5 μm and preferably 1.3 μm to 2.5 μm.

The optical device may have, adjacent to or directly in the exit opening, an inlet element, which focuses the measuring radiation exiting from the exit opening into the measuring point. This outlet element may be configured as a convergent lens, with the focal point of this convergent lens coinciding with the measuring point. It is also possible as an alternative that the outlet element is configured as a spherical or parabolic outlet mirror, whose focal point now coincides with the measuring point.

In a preferred embodiment, the optical device may have a focusing element, for example, in the form of a convergent lens, which converts scattered radiation generated in the measuring point and falling in through the outlet element into a parallel ray bundle, the optical device having a semitransparent mirror, which is arranged such that the parallel ray bundle falls on the mirror and is partially reflected to the outlet and that measuring radiation falling in through the inlet of the optical device falls through the focusing element. Due to this configuration, it is achieved in the optical device in a simple manner that the measuring radiation is focused at the measuring point, on the one hand, and that the scattered radiation generated there reaches the outlet point, on the other hand, the measuring radiation and the scattered radiation run partially along the same optical path.

As an alternative, the optical device may have a focusing element, configured, e.g., as a convergent lens, which converts scattered radiation generated in the measuring point and falling through the outlet element into a parallel ray bundle, wherein the optical device has a first convergent lens device and a second convergent lens device, wherein the first convergent lens device and the second convergent lens device are arranged such that the parallel ray bundle falls on the first and second convergent lens devices, wherein the focal point of the first convergent lens device, which is located on the side of the first collector lens device facing away from the focusing element, forms the inlet of the optical device, and wherein the focal point of the second convergent lens device, which is located on the side of the convergent lens device facing away from the focusing element, forms the outlet point of the optical device. It is achieved in a simple manner that the measuring radiation and the scattered radiation can extend partially along the same path in this embodiment as well.

Finally, it is advantageous for determining the blood alcohol concentration if the light source generates measuring radiation in the infrared or near infrared range. This can be achieved, for example, by a laser, which irradiates a doped emitter element. In addition, it is conceivable that the light source has a laser and a doped light guide, via which the laser is connected to the inlet of the optical device.

The present invention will be explained below on the basis of a drawing showing an exemplary embodiment, which is only a preferred exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
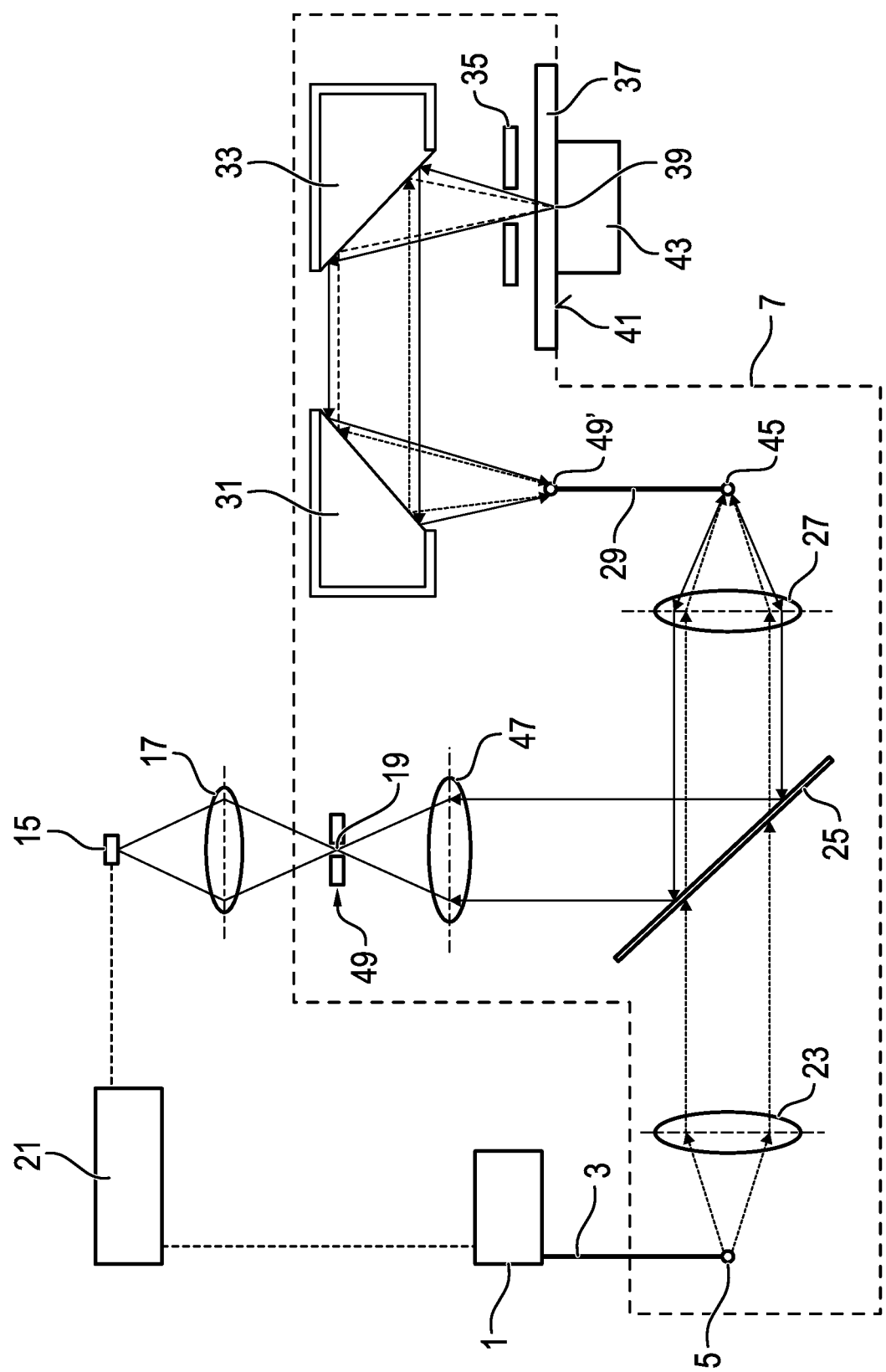
FIG. 1 is a schematic view showing a first exemplary embodiment of a system according to the present invention.

Referring to the drawings, FIG. 1 shows a first exemplary embodiment of a system according to the present invention for the transcutaneous measurement of the blood alcohol concentration. The system has a light source 1, which is connected to the inlet 5 of an optical device 7 by means of a light guide 3. The light source 1 is configured to emit a measuring radiation, the radiation in the exemplary embodiments being described in this case being radiation from the near infrared range, i.e., the wavelengths are between 0.7 μm and 3 μm.

Figure 3B:
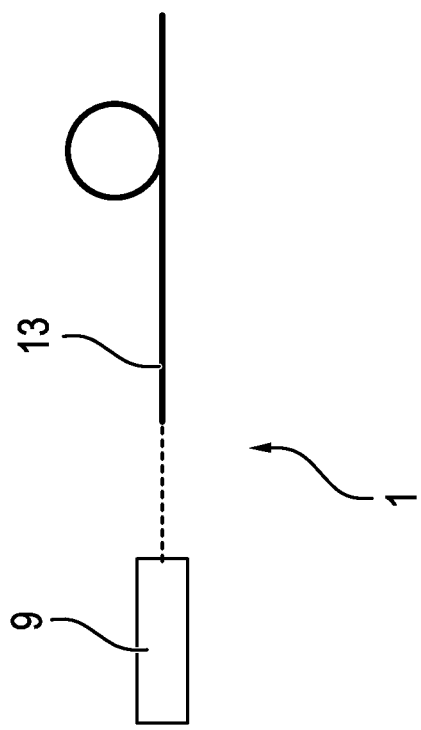
FIG. 3b is a schematic view showing another of two forms of light sources for exemplary embodiments from FIGS. 1 and 2.
Figure 3A:
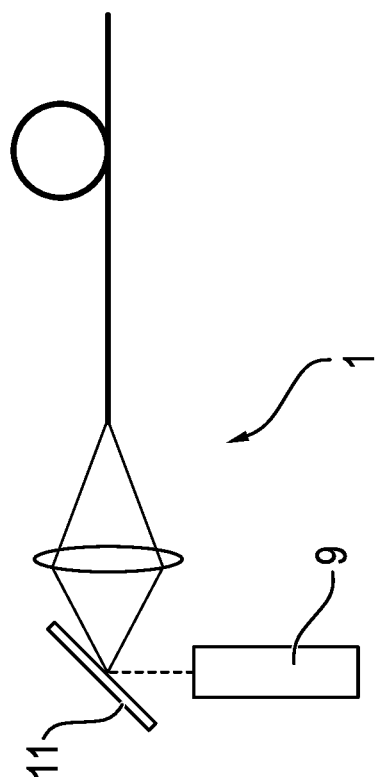
FIG. 3a is a schematic view showing one of two forms of light sources for exemplary embodiments from FIGS. 1 and 2.

To achieve this, the light source 1, as is shown in FIG. 3a, may have a laser 9, which irradiates an emitter 11, which is, in turn, coated with a ceramic powder. This may be doped with Nd, Yb, Er, Tm, Ho, Cr, Co or Ti, which causes the emitter 11 to emit infrared radiation in the above-mentioned wavelength range. As an alternative, the light source 1 may also be configured, as is shown in FIG. 3b, in such a manner that the radiation of a laser 9 is coupled into a doped light guide 13, said light guide 13 being able to be doped with the elements mentioned in connection with the emitter 11.

The system shown in FIG. 1 has, in addition, a detector device 15, in front of which a lens device 17 is arranged such that scattered radiation focused by the optical device 7 in an outlet point 19 is further focused onto the detector device 15, so that this can detect the scattered radiation. The detector device 15 is configured such that it emits a spectrum of at least one part of the detected scattered radiation. The detector device 15 may be configured in this case as a grating spectrometer or as a Fabry-Perot interferometer or as a Fourier transformation spectrometer (FTS or FTIR in English). In addition, the detector device 15 is able to bring about the spectral resolution of the scattered radiation in a wavelength range of 0.7 μm to 3.5 μm and preferably 1.3 μm to 2.5 μm.

Both the light source 1 and the detector device 15 are connected to a computer 21, so that both the light source 1 and the detector device 15 can be actuated by the computer 21 and the computer 21 can analyze the spectra emitted by the detector device 15.

The optical device 7 has a convergent lens 23, which is directed towards the inlet 5 and whose focal point coincides with the inlet 5, so that measuring radiation arriving from the light source 1 is converted into an essentially parallel ray bundle, which will then fall on a focusing element likewise configured as a convergent lens 27 through a semitransparent mirror 25. The measuring radiation is focused further by the convergent lens 27 and is sent by means of a light guide 29 to the focal point of a first spherical or elliptical or parabolic mirror 31. The radiation exiting from the first mirror 31 falls on a second spherical or elliptical or parabolic mirror 33, which acts as an outlet element or outlet mirror and focuses the measuring radiation through an exit opening 35 and a contact surface element 37 of the optical device 7 into a measuring point 39. On the side facing away from the optical device 7, the contact surface element 37 has a contact surface 41, with which a body part 43, shown only schematically, can be in contact such that it is located opposite the exit opening 35. The second mirror 33 is arranged relative to the contact surface 41 such that the measuring point 39 lies on the side of the contact surface element 37 facing away from the optical device 7 at a predefined distance from the contact surface 41. It is achieved due to this configuration that the measuring point 39, in which the measuring radiation is focused, is located at a distance from the surface of the body part 43 when the latter is in contact with the contact surface 41. The distance between the measuring point 39 and the contact surface 41, measured at right angles to the contact surface 41, is preferably between 0.1 mm and 3 mm and especially preferably between 0.5 mm and 1 mm.

When the light source 1 emits measuring radiation, this falls upon the exit opening 35 and is focused, as was already described, to the measuring point 39 at a distance from the skin surface of the body part 43 of a test subject, so that characteristic scattered radiation is generated especially in the area of the measuring point 39. This scattered radiation passes back into the optical device 7 through the exit opening 35, is focused through the mirrors 31, 33 and is sent to the focal point 45 of the convergent lens 27 by means of the light guide 29. The scattered radiation is converted by the focusing element configured as a convergent lens 27 into a parallel ray bundle and the parallel ray bundle falls onto the semitransparent mirror 25, which casts a part of the scattered radiation to another convergent lens 47. This convergent lens 47 focuses the parallel ray bundle scattered radiation into the outlet point 19 arranged in an outlet 49 of the optical device 7, where the focused scattered radiation is detected by the detector device 15 in the already described manner.

The measuring radiation is thus focused in this exemplary embodiment at a point located at a spaced location from the skin surface, so that essentially the radiation generated there is analyzed. This point or the corresponding distance from the contact surface can be selected to be such that the measuring radiation is focused where a sufficient density of blood vessels is present, i.e., the dermis or the subcutaneous tissue, so that a signal sufficient for the concentration measurement of a substance in the blood is generated, i.e., absorption bands are identified in the scattered radiation corresponding to the concentration in question of a substance in the blood can be determined by comparison of measured spectra.

At the same time, the optical device 7 is configured such that precisely the scattered radiation generated in the measuring point 39 is focused at the outlet point 19 and is thus detected by the detector device 15, while precisely scattered radiation generated at other depths is not collected in this point but can hardly pass through the outlet 49' acting as a diaphragm. It is thus ensured that the system is adapted for the blood alcohol concentration measurement by selecting the distance of the measuring point 39 from the contact surface 41 and high accuracy can be reached.

Figure 2:
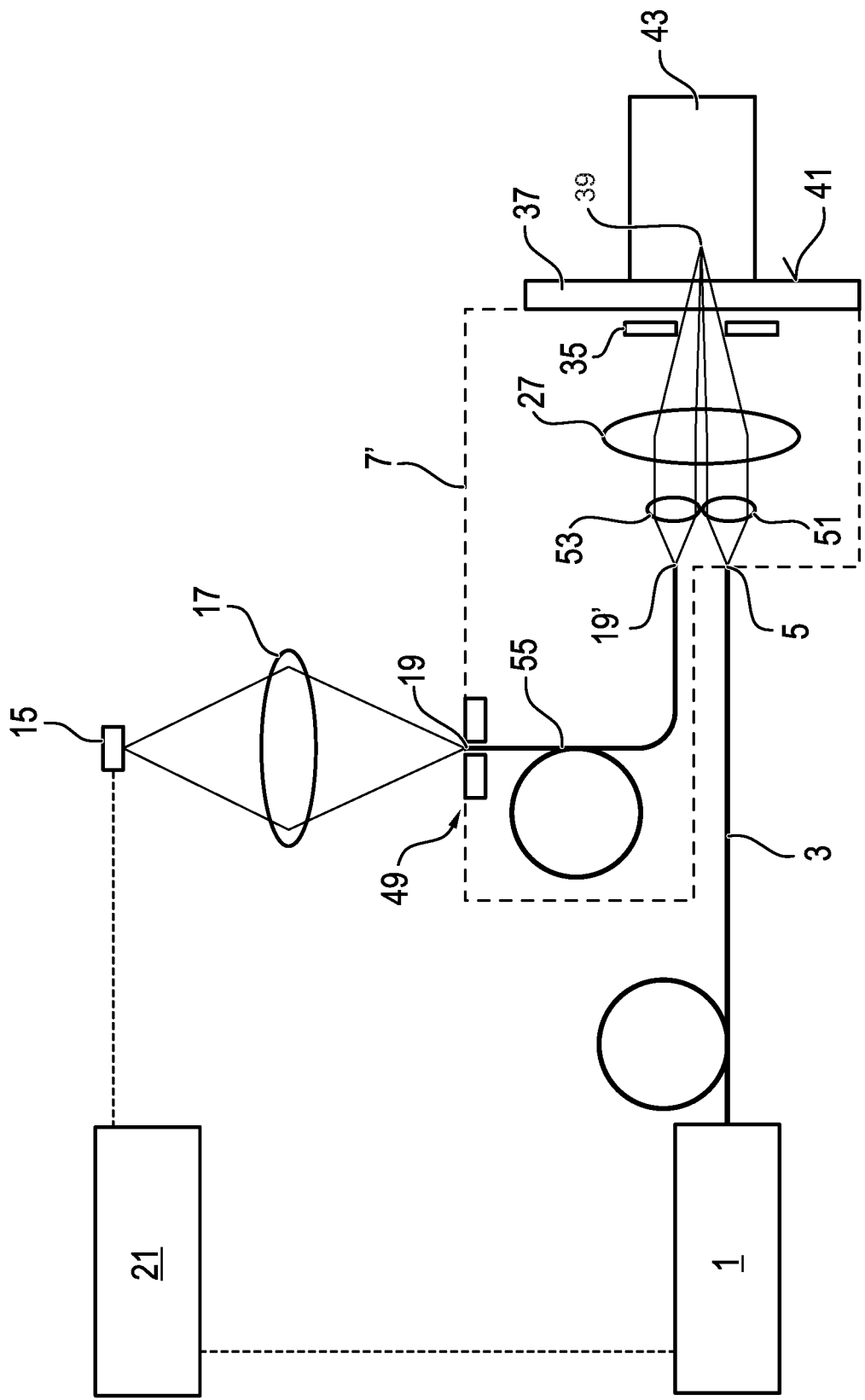
FIG. 2 is a schematic view showing a second exemplary embodiment of a system according to the present invention.

FIG. 2 shows a second exemplary embodiment of a system according to the present invention, in which elements that correspond to elements from the first exemplary embodiment, are designated by identical reference numbers.

A light source 1, which may be configured as described in connection with FIG. 3, is likewise provided in this second exemplary embodiment. The light source 1 is connected via a light guide 3 to the inlet 5 of an optical device 7'. In addition, this exemplary embodiment also has a detector device 15, which may be configured as described in the first exemplary embodiment. The detector device 15 may consequently be configured especially as a grating spectrometer or a Fabry-Perot interferometer and bring about the spectral resolution of the wavelength range of 0.7 µm to 3.5 µm and preferably 1.3 µm to 2.5 µm. A lens device 17 is, in turn, arranged in front of the detector device 15 such that scattered radiation focused by the optical device 7' is further focused onto the detector device 15 in a point 19' at the outlet 49 of the optical device 7', so that this detector device 15 can detect the scattered radiation.

The light source 1 and the detector device 15 are connected to a computer 21 in this case as well, so that this can actuate the light source 1 and perform the further analysis of the spectra of the scattered radiation, which are sent by the detector device 15.

The inlet 5 of the optical device 7' is located in the focal point of a first convergent lens 51, so that the incident measuring radiation is cast by the first convergent lens 51 as an essentially parallel ray bundle onto a focusing element likewise configured as a convergent lens 27. The convergent lens 27 or the focusing element is also the outlet element of the optical device 7' in this exemplary embodiment and the outlet element focuses the measuring radiation, so that the measuring radiation falls through an exit opening 35 and a contact surface element 37. The measuring radiation is focused by the convergent lens 27 in a measuring point 39 in this case as well, and said measuring point is located at a predefined distance from the contact surface 41 on the side of the contact surface element 37 facing away from the optical device 7'. In case of a body part 43 being in contact with the contact surface 41, the measuring point 39 is thus located at a spaced location from the skin surface, and this distance is preferably between 0.1 mm and 3 mm and preferably between 0.5 mm and 1 mm.

Scattered radiation generated in the area of the measuring point 39 falls through the exit opening 35 back into the optical device 7' and is converted by the convergent lens 27 into a parallel ray bundle. In addition, the optical device 7' has a second convergent lens 53, on which falls, just as on the first convergent lens 51, the parallel scattered radiation bundle generated by the outlet or focusing element configured as a convergent lens 27. The second convergent lens 53 focuses the parallel radiation bundle into the outlet point 19' of the optical device 7', which outlet point 19' represents the focal point, and the radiation is conveyed from outlet point 19', by means of a light guide 55, to the point 19, at which it is detected by the detector device 15. The focal point of the second convergent lens 53, which is located on the side of the second convergent lens 53 facing away from the focusing element 27, thus forms the outlet point 19' of the optical device 7'.

Thus, the optical device 7' of this second exemplary embodiment is also configured such that scattered radiation generated in the measuring point 39 and entering the exit opening 35 is focused at an outlet point 19 or 19' at the outlet 49.

It is thus also achieved in the second exemplary embodiment that the measuring radiation is focused at a measuring point 39 located at a spaced location from the contact surface 41 and only the scattered radiation from the area of the measuring point 39 is focused at the outlet point 19 and 19' and detected by the detector device 15. Therefore, this exemplary embodiment is also sensitive only at a depth predetermined by the outlet element or the convergent lens 27, at a spaced location from the skin surface of the test subject.

While specific embodiments of the invention have been shown and described in detail to illustrate the application of the principles of the invention, it will be understood that the invention may be embodied otherwise without departing from such principles.

The invention claimed is:

1. A system for a transcutaneous measurement of a concentration of a substance in blood, the system comprising:
   a light source configured to emit a measuring radiation;
   a detector device configured to detect a scattered radiation;
   an optical device comprising a focusing device, an inlet, an outlet and an exit opening;
   a computer; and
   a contact surface element with a contact surface, wherein:
   the contact surface element is arranged such that the measuring radiation exiting the exit opening falls through the contact surface element;
   the contact surface is provided on a side of the contact surface element facing away from the optical device;
   the inlet of the optical device is arranged such that the measuring radiation emitted by the light source falls on the inlet of the optical device;
   the optical device is configured such that the measuring radiation emitted by the light source and entering the inlet exits through the exit opening and is focused via the focusing device in a measuring point on the side of the contact surface element facing away from the optical device at a predefined distance from the contact surface;
   the optical device is configured such that the scattered radiation generated at the measuring point and entering the exit opening is focused in an outlet point at the outlet;
   the scattered radiation passes directly from the contact surface element through the exit opening to the focusing device such that the focusing device directs the scattered radiation to a single focused radiation location;
   the detector device is arranged such that the detector device detects the scattered radiation focused at the outlet point;
   the detector device comprises a grating spectrometer, a Fabry-Perot interferometer or a Fourier transformation spectrometer;
   the optical device has an outlet element, which focuses the measuring radiation exiting the exit opening to the measuring point;
   the measuring radiation is focused by the focusing device prior to the measuring radiation being focused at the measuring point of the optical device;
   the outlet element is configured as a spherical, elliptical or parabolic outlet mirror;
   a focal point of the the spherical, elliptical or parabolic outlet mirror coincides with the measuring point;
   the outlet element is located opposite the measuring point, the contact surface element and the exit opening;
   the spherical, elliptical or parabolic outlet mirror comprises a longitudinal axis;
   the spherical, elliptical or parabolic outlet mirror is axially opposite another spherical, elliptical or parabolic mirror with respect to the longitudinal axis;
   the focusing device comprises the another spherical, elliptical or parabolic mirror;
   the scattered radiation is directed to the focused radiation location via at least the another spherical, elliptical or parabolic mirror; and
   the computer is configured to determine a blood alcohol concentration based on the scattered radiation detected by the detector device.

2. A system in accordance with claim 1, wherein the detector device is set up to output a spectrum of at least part of the detected scattered radiation.

3. A system in accordance with claim 2, wherein the detector device is configured to bring about spectral resolution of the scattered radiation in the wavelength range of 0.7 μm to 3.5 μm.

4. A system in accordance with claim 1, wherein the outlet element is configured as a convergent lens and wherein a focal point of the convergent lens coincides with the measuring point.

5. A system in accordance with claim 1, wherein a distance of the measuring point from the contact surface, measured at right angles to the contact surface, is between 0.1 mm and 3 mm.

6. A system in accordance with claim 1, wherein the light source generates the measuring radiation in the infrared or near infrared range.

7. A system in accordance with claim 6, wherein the light source has a laser and a doped emitter element.

8. A system in accordance with claim 6, wherein the light source has a laser and a doped light guide.

9. A system in accordance with claim 1, wherein the detector device is configured to bring about spectral resolution of the scattered radiation in the wavelength range of 0.7 μm to 3.5 μm.

10. A system in accordance with claim 1, wherein the detector device is configured to bring about spectral resolution of the scattered radiation in the wavelength range of 1.3 μm to 2.5 μm.

11. A system in accordance with claim 1, wherein a distance of the measuring point from the contact surface, measured at right angles to the contact surface, is between 0.5 mm and 1 mm.

12. A system in accordance with claim 1, wherein the computer is connected to both the light source and the detector device and configured to actuate the light source and the detector device and configured to analyze the scattered radiation detected by the detector device to determine the blood alcohol concentration.

13. A system in accordance with claim 12, wherein the computer is configured to analyze a spectra of the scattered radiation detected by the detector device, wherein the computer is configured to determine the blood alcohol concentration based on the spectra of the scattered radiation.

14. A system in accordance with claim 13, wherein the computer is configured to analyze absorption bands of the scattered radiation detected by the detector device in a wavelength range of 0.7 μm to 3.5 μm.

* * * * *